(12) United States Patent
Ingold et al.

(10) Patent No.: US 9,101,336 B2
(45) Date of Patent: Aug. 11, 2015

(54) MEDICAL SYMBOL KEYPAD

(76) Inventors: Sandra Ingold, Crestline, CA (US);
Melody Czanstkowski, Crestline, CA (US)

( * ) Notice: Subject to any disclaimer, the term of this patent is extended or adjusted under 35 U.S.C. 154(b) by 402 days.

(21) Appl. No.: 13/594,797

(22) Filed: Aug. 25, 2012

(65) Prior Publication Data

US 2014/0055359 A1 Feb. 27, 2014

(51) Int. Cl.
*G06F 3/02* (2006.01)
*A61B 5/00* (2006.01)
*G06F 3/023* (2006.01)
*G06F 3/038* (2013.01)

(52) U.S. Cl.
CPC .............. *A61B 5/7475* (2013.01); *G06F 3/023* (2013.01); *G06F 3/0219* (2013.01); *G06F 3/038* (2013.01)

(58) Field of Classification Search
CPC ....... G06F 1/662; G06F 3/0219; G06F 3/023; G06F 3/038; A61B 5/7475
USPC .......................................................... 345/168
See application file for complete search history.

(56) References Cited

U.S. PATENT DOCUMENTS

2007/0188472 A1* 8/2007 Ghassabian .................. 345/169
2008/0106440 A1* 5/2008 Verma et al. ..................... 341/22

* cited by examiner

*Primary Examiner* — Andrew Sasinowski

(57) ABSTRACT

The present invention is a medical symbol keypad that includes a plurality of keys that each have a top surfacing that are disposed on the medical symbol keypad and a plurality of medical symbols that are disposed on the top surfacing of the keys. The medical symbol keyboard includes a software module that is included with the medical symbol keypad, the software module performs a plurality of operations associated with the medical symbol keypad and a downloadable App that is similar to the software module provided on the medical symbol keypad.

7 Claims, 1 Drawing Sheet

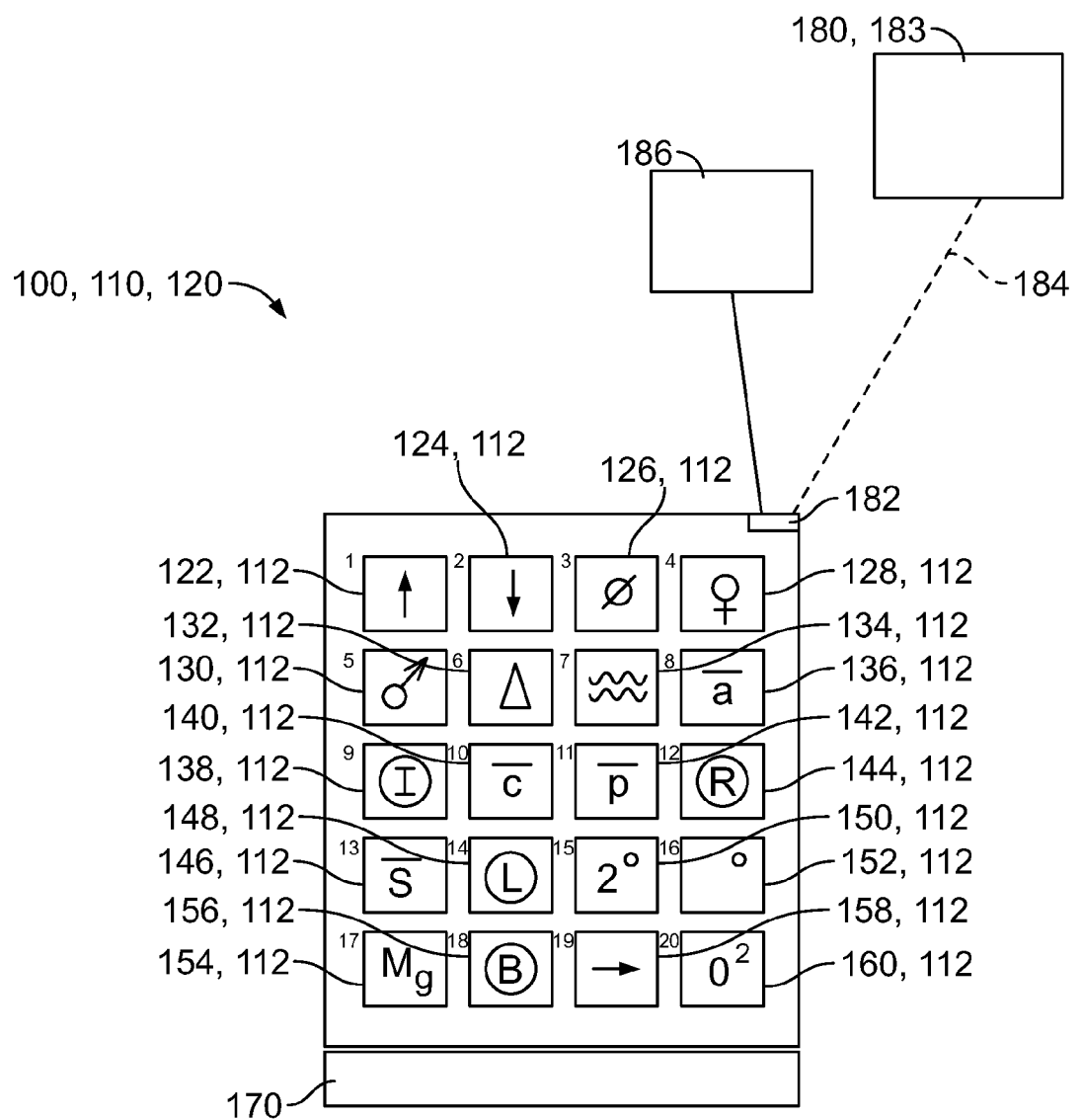

MEDICAL SYMBOL KEYPAD

TECHNICAL FIELD & BACKGROUND

Currently there is a lack of computing options that cater precisely to the medical industry. Data recording professionals, when attempting to transcribe universal notations from a patient's file to an electronic source, often have to type an entire word out due to the inability to define medical symbols on a conventional keyboard.

The present invention generally relates to a keypad. More specifically, the invention is a medical symbol keypad.

It is an object of the invention to provide a medical symbol keypad that contains 20 keys that represent 27 routinely used medical words.

It is an object of the invention to provide a medical symbol keypad that provides relatively faster input of medical information.

It is an object of the invention to provide a medical symbol keypad that is compatible with IDevices, LINUX™ and WINDOWS™ platforms.

What is really needed is a medical symbol keypad that contains 20 keys that represent 27 routinely used medical words that provide relatively faster input of medical information that is compatible with IDevices, LINUX™ and WINDOWS™ platforms.

BRIEF DESCRIPTION OF THE DRAWINGS

The present invention will be described by way of exemplary embodiments, but not limitations, illustrated in the accompanying drawings in which like references denote similar elements, and in which:

FIG. 1 illustrates a front view of a medical symbol keypad, according to an embodiment of the present invention.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is utilized repeatedly. The phrase generally does not refer to the same embodiment, however, it may. The terms "comprising", "having" and "including" are synonymous, unless the context dictates otherwise.

FIG. 1 illustrates a front view of a medical symbol keypad 100, according to an embodiment of the present invention.

The medical symbol keypad 100 includes a plurality of keys 110 and a plurality of medical indicia 120. The medical symbol keypad 100 is approximately 4 inches in length and 3 inches in width but can have any suitable dimensions. The keys 110 include approximately 20 keys but can include 10 keys, 30 keys, 40 keys or any suitable number of keys. The keys 110 each have a top surfacing 112 and are disposed on the medical symbol keypad 100. The medical indicia 120 are a plurality of medical symbols 122 disposed on the top surfacing 112 of the keys 110. There are approximately 20 medical symbols 120 that correspond to each of the 20 keys 110 with one medical symbol 120 exclusively corresponding to one key 110.

The medical symbols 120 include an increase symbol 122, a decrease symbol 124, a none symbol 126, a female symbol 128, a male symbol 130, a change symbol 132, an approximate symbol 134, a before symbol 136, an independent symbol 138, a with symbol 140, an after symbol 142, a right symbol 144, a without symbol 146, a left symbol 148, a due to (or a 2 hours) symbol 150, an hours (or a degree) symbol 152, a microgram symbol 154, a both symbol 156, a next (or a then) symbol 158 and an oxygen symbol 160. The 20 medical symbols 120 can be utilized to form approximately 27 words or any other suitable number of words. The increase symbol 122 is utilized to indicate an increase in something such as a quantity of a medication or other suitable increase. The decrease symbol 124 is utilized to indicate a decrease in something such as a quantity of a medication or other suitable decrease. The none symbol 126 is utilized to indicate none of something is utilized or needed, such as not having a need for a medical procedure. The female symbol 128 is utilized to indicate that a female is involved in utilizing the female symbol 128. The male symbol 130 is utilized to indicate that a male is involved in utilizing the male symbol 130. The change symbol 132 is utilized to indicate that a change is needed when utilizing the change symbol 132. The approximate symbol 134 indicates that an approximate or approximately a quantity or other suitable use of something is needed. The before symbol 136 indicates that something should be utilized before something else or any other suitable before utilization. The independent symbol 138 indicates the utilization of the word independent in a suitable context. The with symbol 140 is utilized to indicate that something is suitably with something else such as a medication is taken with water before bedtime or some other suitable application. The after symbol 142 indicates that something should be utilized after something else or any other suitable after utilization. The right symbol 144 is utilized to indicate that the word right should be suitably utilized, such as a right arm or other suitable right body part. The without symbol 146 indicates that the word without should be utilized in a suitable context such as taking a medication without a dairy food. The left symbol 148 indicates that the word left should be suitably utilized, such as a left arm or other suitable left body part. The due to symbol 150 can also be an or 2 hours symbol 150' indicates suitable utilization of the words due to or 2 hours. The a hours (or a degree) symbol 152 is indicated to utilize a quantity of hours or a quantity of degrees. The microgram symbol 154 indicates utilization of the quantity of micrograms such as 100 micrograms of a dosage. The both symbol 156 is indicated to utilize the word both in a suitable context such as taking both medication A and medication B. The next (or a then) symbol 158 indicates the utilization of the word next or then in a suitable context such as returning for an appointment next week. The oxygen symbol 160 indicates the use of oxygen in a suitable setting such as utilizing oxygen to keep a patient breathing.

The medical symbol keypad 100 additionally includes a software module 170 and a downloadable App 180. The software module 170 is included with the medical symbol keypad 100 and performs a plurality of operations associated with the medical symbol keypad 100 such as applying the medical symbols 120 when the corresponding keys 110 are depressed. The downloadable App 180 is similar to the software module 170 provided on the medical symbol keypad 100 and can be downloaded onto the medical symbol keypad through a USB port 182 or online from the Internet 184 from an online source 183 or downloaded from an App store 186.

The medical symbol keypad relatively clearly and effectively provides for relatively faster universal input of medical information. The medical symbol keypad is a condensed, single button per work structure. The medical symbol keypad contains twenty keys that represent twenty-seven routinely used medical related words. The medical symbol keypad will allow medical professionals to type documents the way they are handwritten. The medical symbols are universal and will not have to be translated into any other language. Currently, when transcribing, the words for the medical symbols have to be spelled out in the language of the transcriber. The medical symbols are universal as is the medical terminology.

The medical symbol keypad has five variations:
1. An App that would allow a user to bring up a specialized keyboard that has the symbols for medical shorthand as well as standard keyboard symbols for entry into a text field.
2. Software that would be a pop-up, like a calculator.
3. Software as an on-screen keyboard with the number pad on the right being replaced by the symbols of the medical symbol keypad.
4. Hardware that would be an accessory device that plugs into a USB port on a computer or an existing keyboard.
5. A specialized keyboard with the number pad on the right of the keyboard being replaced by the symbols of the medical symbol keypad.

The medical symbol keypad will reduce input time due to striking one key versus spelling out an entire word. It will also be relatively more accurate data input and will eliminate any need for translation and increases typing speed and accuracy. The medical symbol keypad will be relatively significantly beneficial when the medical field achieves the goal of becoming paperless.

The medical symbol keypad is a universal computing medium that introduces a well-suited approach to transferring medical documents. Made of relatively high quality materials, the medical symbol keypad is a single button corresponding key instrument representing approximately twenty icons relative to medical terminology. Intended to offer usage that includes an application for specialized keyboarding, two software options for downloading into an existing computer, a USB connection support hardware option and a physical adaptation of a current traditional keyboard where the number pad is replaced with its design, the medical symbol keypad permits a recorder to simply press the correct image associated with communicating a definitive practice, direction, identifier and/or measurement. The medical symbol keypad may be readily available at renowned electronic and industry support retailers.

The medical symbol keypad may eliminate translating errors while improving upon data recording speeds and accuracy. The feature of a twenty-key icon specific computing device, offering compatibility with iDevices, LINUX™ and WINDOW™ platforms, may afford users with an effective and innovative accessory to maintaining electronic records.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

The invention claimed is:

1. A medical symbol keypad, comprising:
    a plurality of keys that each have a top surfacing, said keys are disposed on said medical symbol keypad;
    a plurality of medical indicia that include a plurality of medical symbols, said medical symbols are disposed on said top surfacing of said keys, said medical symbols include an increase symbol, a decrease symbol, a none symbol, a female symbol, a male symbol, a change symbol, an approximate symbol, a before symbol, an independent symbol, a with symbol, an after symbol, a right symbol, a without symbol, a left symbol, a selected one of a due to and a 2 hours symbol, a selected one of an hours and a degrees symbol, a Mg symbol, a both symbol, a selected one of a next and a then symbol and an oxygen symbol; and
    said plurality of keys configured to enable input operations for medical symbol related data.

2. The medical symbol keypad according to claim 1, wherein said keys include 20 keys.

3. The medical symbol keypad according to claim 2, wherein said medical symbols include 20 medical symbols.

4. The medical symbol keypad according to claim 3, wherein said 20 medical symbols correspond to each of said 20 keys with one said medical symbol exclusively corresponding to one said key.

5. The medical symbol keypad according to claim 1, wherein said medical symbols are utilized to form approximately 27 words.

6. The medical symbol keypad according to claim 1, wherein said plurality of keys are configured to apply medical symbol related data to the upon the depression of at least one of said plurality of keys.

7. The medical symbol keypad according to claim 1, additionally comprising a USB port.

* * * * *